Dec. 1, 1942. C. FIORE Plant Pat. 558
GERANIUM
Filed March 19, 1942
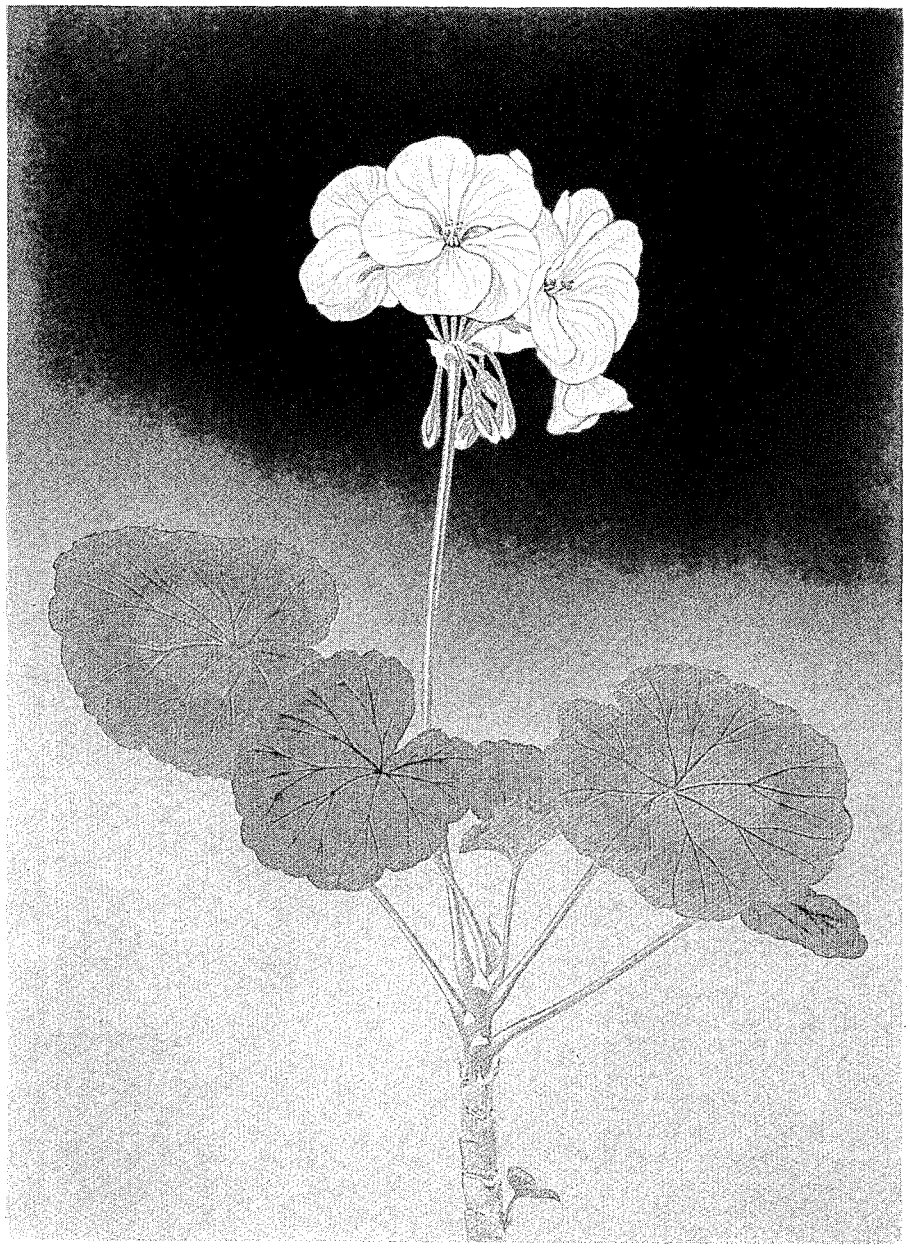
INVENTOR.
Charles Fiore
BY
Lyman Latta Attorney Patented Dec. 1, 1942

Plant Pat. 558

UNITED STATES PATENT OFFICE

558

GERANIUM

Charles Fiore, Highwood, Ill.

Application March 19, 1942, Serial No. 435,308

1 Claim. (Cl. 47—60)

My new variety pertains to white geraniums and is the result of cross-pollination between the pale pink Lady Jane variety as the seed parent and a double white cream colored variety, White Lady, as the pollen parent. My new variety was discovered in the spring of 1937 as a seedling resulting from this cross-pollination. I have since propagated my variety by slips and have found the novel characteristics of my novel variety to be firmly fixed. It has been found impossible to propagate my variety by seed and so all propagation must be asexual.

In the so called "white geraniums" available prior to my discovery, the flowers have either a definite pinkinsh cast or have a greenish tinge in the hearts of the florets upon first opening. In contrast, my improved variety produces flowers that are pure white throughout, from the time of the first opening. This is the most outstanding, but not the only characteristic which, in combination, distinguish my improved variety from others. Such distinguishing characteristics are as follows:

Growth habits: The growth is more upright than spreading. My variety will attain a full growth of eighteen inches in two years, but does not grow substantially taller than eighteen inches.

Foliage: The foliage is darker green than that of the parents. It is clean and abundant. When the plant is young the leaves are set fairly close to the stalk on short stems which lengthen as the plant grows older.

Flower: The bud is pure white in color, having no tint in the throat as the floret opens. The individual florets are as large as silver dollars, and larger than those of any known variety of geranium. The flower stems are long, from six to eight inches in length. The color of the full blown flower is white, with no discernible tint of any color. The florets are single, with orange-red stamens.

Blooming habits: My improved variety blooms freely and continuously. If properly nurtured, the plant will bloom thus indefinitely. I have carefully observed specimens of my variety which have, under cultivation in a greenhouse, with periodic enlargement of pot volume, bloomed continuously for two years, with a continuous throwing of side branches. As to longevity, I have found that the bloom clusters will endure for from three to five weeks, longer than the average for other varieties of geranium.

My improved variety is relatively free from fungus and other disease.

The original illustration accompanying this application shows in approximately their true colors, the upper portions, including the blooms, of my improved variety.

I claim:

The new and distinct variety of geranium with qualities in combination substantially as shown and described, characterized particularly by the pure white color of its flowers, the large size of the individual florets, the continuous bloom, the longevity of bloom of the individual bloom clusters, the length of the flower stems, the dark green, clean and abundant foliage, and the tendency of the plant not to grow taller than eighteen inches.

CHARLES FIORE.